United States Patent
Cheng et al.

[11] Patent Number: 5,876,942
[45] Date of Patent: Mar. 2, 1999

[54] PROCESS FOR SEXING COW EMBRYOS

[75] Inventors: Winston Teng-Kuei Cheng, Taipei; Chuan-Mu Chen, Tai Chung; Che-Lin Hu, Taipei; Chih-Hua Wang, Taipei; Kong-Bung Choo, Taipei, all of Taiwan

[73] Assignee: National Science Council of Republic of China, Taipei, Taiwan

[21] Appl. No.: 899,811

[22] Filed: Jul. 24, 1997

[51] Int. Cl.[6] .............................. C12Q 1/68; C07H 21/02; C07H 21/04
[52] U.S. Cl. ............................... 435/6; 536/231; 536/24.3
[58] Field of Search ............................. 435/6; 536/23.1, 536/24.3; 985/77, 78

[56] References Cited

U.S. PATENT DOCUMENTS 5,578,449  11/1996  Frasch et al. ................................ 435/6
5,596,089  1/1997  Silversides et al. ..................... 536/24.3

OTHER PUBLICATIONS

Sommer et al., Nucleic Acids Research 16(6) : 6749 (1989).
Kirkpatrick et al., J. of Reproduction and Fertility 98 : 335–340 (1993).
Pomp et al., J. Animal Science 73 : 1408–1415 (1995).
Aasen et al., BioTechnology 8 : 1279–1281 (1990).
Darling et al., PNAS 83:135–139 (1986).
Gibson et al., Biochemistry 31(35) : 8384–8388 (1992).
Gibson et al., Biochemical and Biophysical Research Communications 174(3) :1306–1312 (1991).
Suzumori et al., Obstetrics & Gynecology 80(1) : 150–154 (1992).
Gibson et al., Biochemistry 30 :1075–1079 (1991).
Shimokawa et al., J. of Biological Chemistry 262(9) : 4042–4047 (1987).
Schafer et al., BioEssays 18(12) :955–962 (1996).
Sullivan et al., BioTechniques 15(4) :636–641 (1993).
Ennis et al., Animal Genetics 25 :425–427 (1994).

*Primary Examiner*—W. Gary Jones
*Assistant Examiner*—Ethan Whisenant
*Attorney, Agent, or Firm*—Bacon & Thomas

[57] ABSTRACT

A rapid, highly reproducible and sensitive technique has been successfully developed for sexing the cow embryos, by method of polymerase chain reaction (PCR) against the amelogenin (bAML) genes located on both X- and Y-chromosomes of the Holstein dairy cattle. Results from DNA sequence analysis showed that there was only 45% homology between the intron 5 of AMLX and AMLY genes. Based on these sequences a pair of sex-specific primers, pbAML5XY(+) and pbAML5XY (−), were designed allowing to amplify a single fragment of 476-bp from the female cattle and two fragments of 476-bp and 341-bp from the male ones, respectively. The most important feature is that the precise sensitivity of sex-determination was confirmed to be reached as minimum template as trace amount of genomic DNA content in either a single lymphocyte or a single blastomere isolated from cow embryo at day-6 to day-7. Moreover, neither those of complicated procedures for purifying the DNA prior the PCR nor any extra pair of primers for serving as internal control is thought to be essential and the sex-determination of over hundred embryos can be completed at once within 4hrs.

7 Claims, 13 Drawing Sheets

```
LOCUS       BOVAMLY       1539 bp ds-DNA              MAM       28-OCT-1995
DEFINITION  Bos taurus chromosome Y amelogenin (AMLY) gene, complete intron 5.
ACCESSION   L48609
KEYWORDS    amelogenin.
SOURCE      Bos taurus (strain Holstein) adult blood DNA.
  ORGANISM  Bos taurus
            Eukaryota; Animalia; Chordata; Vertebrata; Mammalia; Theria;
            Eutheria; Artiodactyla; Ruminantia; Pecora; Bovidae; Bovinae;
            Bovini.
REFERENCE   1 (bases 1 to 1533)
  AUTHORS   Cheng,W.T.K., Chen,C.-M., Hu,C.-L., Wang,C.-H. and Choo,K.-B.
  TITLE     Cheng paper
  JOURNAL   Unpublished (1995)
  STANDARD  full staff_review
REFERENCE   2 (sites)
  AUTHORS   Cheng,W.T.K.
  TITLE     [No Title]
  JOURNAL   Unpublished (1995)
  STANDARD  full staff_review
FEATURES             Location/Qualifiers
     intron          1..1539
                     /number=5
                     /map="chromosome Y"
                     /gene="AMLY"
                     /evidence=EXPERIMENTAL
                     /citation=[2]
     source          1..1539
                     /organism="Bos taurus"
                     /strain="Holstein"
                     /cell_type="leukocyte"
                     /dev_stage="adult"
                     /germline
                     /macronuclear
                     /sequenced_mol="DNA"
                     /tissue_type="blood"
BASE COUNT      544 a     216 c     245 g     534 t
ORIGIN
        1 gtaagtacac cttaaggcca tttacaacag ttatgaaaat aatcgagcaa aaatagccca
       61 cagaaatcaa aattctctca cagtccaaga cctagagttt caactgcagt tagtgattct
      121 attattccaa gtgtgtgttg taagtttata aatgagcttg tttatctata tggcatacac
      181 tttgtgaatt caaaatctac aattgtttgg aattttaatg gcaatatgaa ttgctattga
      241 aatgcagtat aataaaggca acaattctta tcttctggtt gcttaactag tacattagac
      301 ttatacagaa ataaataaaa agagtatttc tgggattgag gagaaggaag tatcagtttt
      361 aaaaaattat agctggatct tcaaggctct aaaggaatat tacctgttgt aggtggtttt
      421 aaagtaattt ggaaacagtt aaagtagaca aacgtagatt ctatttcatt cccaggatta
      481 aaaaaaattt taataagaat gtttcataac atagcttaaa atttcctccc cacttcagaa
      541 agcttttggg gaataattga gaagtaaccc aataagggtc accttccatt cattcctgta
      601 aaccctcatt tctctgcatt aagtttagta attctacaat taataaatgc tgttagggat
      661 ttgctactga gaaacactg aagagtaagg tagaaataac ctgaatatat agtcaggata
      721 tgtggcttct attgctagct ctgccctgaa gaagaaattt acagctgttt tcctctaaat
      781 gtttcctcta aattggtttt cctctctcct aaaataagtg aaagtgatca gtttaaaggc
      841 tctttgcaag tatttgtgct tagagtacaa agagtaaaat attttatgtt cattatttaa
      901 aagttaaaat attcaattaa tcaaaatatt ttattattaa atataatttc ccaataaaaa
      961 attttataa accatatcat aatttggta catttatgag aaattgtgac tgtttgaaaa
     1021 ttgattgtat cccaaacatt gtggtaccaa tgactatttc agtctaacct acatgggctc
     1081 tgattaaata gaagatacat ttctttgttc attaacaaat aatgtcatgg aatttacagt
     1141 atgtttatat catgtcaaag atatgcatgt aaagatgctc tggttaggta aactcttaaa
     1201 atttcatttc tgcttctgga aaattaggat aaatggatct tcttagaatt atttatagaa
     1261 aatgataata aattattaac tattagggac agattaatta taagtctgtc aagcaggcaa
     1321 aggtcagaaa aaaatcggtg tgttactcaa attatcgatg gttgtaaagg ttttaaagca
     1381 gggctgccca catagacact tcaaatataa tgataaagtg acaaacctt tggaaattat
     1441 aaatttttaac ttactggtta ccatcttttc tagtaaaact gaagatggat tctctagtaa
     1501 tatttgtaaa ttacatgttc attttgtttt tttcccccag
```

FIG. 3

```
LOCUS       BOVAMLX      1684 bp ds-DNA              28-OCT-1995
DEFINITION  Bos taurus X chromosome amelogenin (AMLX) gene, complete intron 5.
ACCESSION   L48608
KEYWORDS    amelogenin.
SOURCE      Bos taurus (strain Holstein) adult blood DNA.
  ORGANISM  Bos taurus
            Eukaryota; Animalia; Chordata; Vertebrata; Mammalia; Theria;
            Eutheria; Artiodactyla; Ruminantia; Pecora; Bovidae; Bovinae;
            Bovini.
REFERENCE   1  (bases 1 to 1684)
  AUTHORS   Cheng,W.T.K., Chen,C.-M., Hu,C.-L., Wang,C.-H. and Choo,K.-B.
  TITLE     Cheng paper
  JOURNAL   Unpublished (1995)
  STANDARD  full staff_review
REFERENCE   2  (sites)
  AUTHORS   Cheng,W.T.K.
  TITLE     [No Title]
  JOURNAL   Unpublished (1995)
  STANDARD  full staff_review
FEATURES             Location/Qualifiers
     intron          1..1684
                     /number=5
                     /map="chromosome X"
                     /gene="AMLX"
                     /evidence=EXPERIMENTAL
                     /citation=[2]
     misc_difference 1..1684
                     /note="65.9% sequence similarity with bovine Y chromosome
                     amelogenin gene (bAMLY gene) intron 5"
                     /citation=[2]
     source          1..1684
                     /organism="Bos taurus"
                     /strain="Holstein"
                     /cell_type="leukocyte"
                     /dev_stage="adult"
                     /germline
                     /macronuclear
                     /sequenced_mol="DNA"
                     /tissue_type="blood"
BASE COUNT      542 a    265 c    327 g    550 t
ORIGIN
        1 gtgagtatac cttgaggtca ctacaacact tatgaaaatg gtcgagcgaa aatggccccc
       61 ccagagattg aaaatctctc acagtccaag gcctacagtt tcagtagcta cagctacagc
      121 tcagtgattc agttagccca agtgtgtgct gtaagtttat attataaaga gttcatctat
      181 atggcttaga attaacacaa tagcttttat ggtggacagg gaggcctggc gtgctgcgat
      241 tcatggggtc gtaaagagtc ggacatgact gagctactga tctgatctga tctgaaattc
      301 tataattact ttgaattcct accagaatat ctattattga aacctgttaa ttttacagac
      361 agtactataa gggaacatta gttctcttta tctttcaaag gtttgaccag caataatagg
      421 ctagaattga accggagatt tcttttaaaa gggtaatttt tgccagtgag gggatgcaga
      481 tatttgaaca ggtaggtggg aggtctcttt aaaaacctaa aggaaaatta cttgtttaaa
      541 gtggttttca atctaacttg gaggaagcta aactacacag attgctagat tccttttcag
      601 tgctgggatt ctgtagatta agcttttagc aataagtctt catagtaaag gacaaaatat
      661 cctttcatta cagaaagctc tttcccactc ttccaagtga gtgggaaata gtcaataagt
      721 gacccttatc catatatata aaccctcact tgtgtgtata agagattatg taattctact
      781 gtatgcatgt cttcaaatgt aattccaagc tataaatgtt attaatgatt ttctactgag
      841 aaggtgaggg gtggggtaga aatgacctgg atggggagcc gggatacctg agttccagtt
      901 ataactctgc actcaaaaag gagatgctgt ttaacaagtc acttcaacta tatgggtgtt
      961 tacccgttaa aatgagagga agtaactaaa tcaaataact ttcaagcctt tgtctaagaa
     1021 gaaataccat agttttccaa taaaaattat atgttatata aggcttcaaa attatgggaa
     1081 tatttgtgga gaacacaggc atatttgtgg aaaatatgga gcatatttga aaaatgattg
     1141 tatcccaaat gctctggtgc ctacagttga ttattctagt ctaaggtaca ggttacgtct
     1201 ttgtatagaa aatatgttta tctcgccaaa atgcatttat ctctttatta ataattagtg
     1261 ttatgaactt tataaatctt gccagagcta ttcaaggaaa ggtgattttg ggtacgtagt
     1321 ttgaactctt taaaattccc atctaaaatt agaggtaaat agtgatagca tcttagagtt
     1381 gtcttaagaa aataaagtgt tgagtttaag aaatgaccat gcagaaagta ctcaccccaa
     1441 tacagcaatt gttgttttat tattcaataa ttgtttttaag tattctgaag gcagggcct
     1501 ccatcctgac acctcatatc taatgactat gagacaacaa agaaagtttg tgaattatag
     1561 agttcaactt caatggctat aatattgttt tggcaaaatt gaacccatat ttgttactat
     1621 aaatggtact cactaagaat atttgtaaat tgtttttactt gcttcttttg caattttttt
     1681 ccag
```

```
X GTGAGTATACCTTGAGGTCAC-TACAACACTTATGAAAATGGTCGAGCGAAAATGGCCCCCCAG  64
  || |||| ||||| ||| ||  ||||||| |||||||||| |||||| ||||| ||||   |||
Y GTAAGTACACCTTAAGGCCATTTACAACAGTTATGAAAATAATCGAGCAAAAATAGCCCA--CAG  63
        Upstream sexing primer
       5'-AAATTCTCTCACAGTCCAAG-3'
X AGATTGAAAATCTCTCACAGTCCAAGGCCTACAGTTTCAGTAGCTACAGCTACAGCTCAGTGATT 129
  | ||  ||| |||||||||||||||||| ||||  |||||| ||                |||||||
Y AAATCAAAATTCTCTCACAGTCCAAGACCTAGAGTTTCAACTGCAGTT---------AGTGATT 118

X CAGTTAGCCCAAGTGTGTGCTGTAAGTTTATATTATAAAGAGTTCATCTATATGGCTTAGAATTA 194
  |  |||  |||||||||| ||||||||||||||  |     ||| ||||||||||| || |
Y CTATTATTCCAAGTGTGTGTTGTAAGTTTATAAATGAGCTTGTTTATCTATATGGCATACA---- 179

X ACACAATAGCTTTTATGGTGGACAGGGAGGCCTGGCGTGCTGCGATTCATGGGGTCGTAAAGAGT 259
              ||||
Y ---------CTTTG------------------------------------------------- 184

X CGGACATGACTGAGCTACTGATCTGATCTGATCTGAAAT-----TCTATAATTACTTTGAATTCC 319
                                    ||||     |||| |||| || |||||
Y -----------------------------------TGAATTCAAAATCTACAATTGTTTGGAATTTT 216

X TACCAGAATATCTAT---TATTGAAACCTGTTAATTTTACAGACAGTACTATAAGGG-AACATTA 380
          |||||  ||  ||||||||           |||||  |||| || |||| |
Y AATGGCAATATGAATTGCTATTGAAATG---------------CAGTATAATAAAGGCAACAATT 266

X GTTCTCTTTATCTTTCAAAGGTTTGACCAGCAATA--ATAGGCTAGAATTGAACCGGAGATTTCT 443
   || ||||         ||||      |  | ||   |||  ||   |   |||   |
Y CTTATCTTCT---------GGTTGCTTAACTAGTACATTAGACTTATACAGAAATAAA------- 315

X TTTAAAAGGGTAATTTTTGCCAGTGAGGGGATGCAGATATTTGAACAGGTAGGTGGGAGGTCTCT 508
  ||||| |  |||| ||  | ||||| || | |    |||  |                     |
Y --TAAAAGAGTATTTCTGGGATTGAGGAGAAGGAAGTATCAGT-------------------T 358

X TTAAAAAC--------------------CTAAAGGAAAATTACTTGTTTAAAGTGGTTTTCAA 551
  |||||||             |||||||||| ||||| ||||  | ||||||||| ||
Y TTAAAAAATTATAGCTGGATCTTCAAGGCTCTAAAGGAATATTACCTGTTGTAGGTGGTTTTTAA 423
                                  3'-GATTCCTTTTAATGGACAAC-5'
                                     Downstream sexing primer
```

FIG. 10

PROCESS FOR SEXING COW EMBRYOS

BACKGROUND OF THE INVENTION

1. Field of the Invention

The invention relates to a process for sexing cow embryos and in particular, to a process for sexing cow embryos by method of polymerase chain reaction(PCR) against the amelogenin (bAML) genes located on both X- and Y-chromosomes of the Holstein dairy cattle. The invention further relates to a group of primers useful in such a process for sexing cow embryos and, specificaly, to a pair of sex-specific primers designed for amplify a single fragment of 467-bp from the female cattle and two fragments of 467-bp and 341-bp from the male one , respectively. In addition, the invention also provide a kit for sexing cow embryos.

2. Description of the Prior Art

Recently, as various technigues of animal reproduction are extensively advanced, animal husbandry is not restricted within traditional breeding tasks any more. Among these, the most promising ones are techniques related with embryo transplantation, such as embryo freezing, embryo cloning, embryo sexing and the like; since the intimately combined use of these techniques with embryo transplantation will promote managing efficiencies of animal husbandry, and thereby yields revolutionary benefits.

Several methods can be used for sexing animal embryos at present, including: karyotyping, H-Y antigen analysis, X-chromosome-linked enzymatic activity test, Y-specific probe hybridization, polymerase chain reaction method and the like (Bondioli el al., Theriogenology 31: 95–104, 1989).

The karyotyping method is relied principally on cytogenetic analysis against blastomeres of a embryo and determines sex type of the embryo on basis of the occuring of X or Y sex chromosomes. The karyotyping method had been developed since 1968, Gardner and Edwards (Nature 218: 346–348 ) observed directly blaetocysts of rabbits and determines the feminality of that rabbit embryo based on the fact that there is an inactivated X chromosome, or so-called Barr's body, existed in that cell, however, according to King (J. Reprod. Fert. 98: 335–340, 1984 ), this method is not suitable for sexing embryos of common domestic animals, since, in somatic cells of common domestic animals, observable Barr's body is less than 50%, and further, cytoplasm of embryo of common domestic animals including embryos of pork, beef, sheep and goat, are not as clear as rabbit embryo such that observation of Barr's body in those embryos is difficult to carry out. At present, karyotyping done on embryos of domestic animals consists usually of treating embryo firstly with chochicine to induce its blastomere in metaphase of cell division and verifying whether there is Y chromosome in the karyotype of the embryo according to the shape of the chromosome. However, sexing embryo based on karyotyping involving treatment with chochicine is subject to have several disadvantages in that its procedure is cumbersome and time consumptive as well as the identifiability of cell is low, and in particular, with single blastomere, the probability to obtain an identifiable karyotype is even smaller.

The X-linked enzymatic activity test is based on the fact that both X chromosomes of normal female mammal have function before the blastula stage in the development of the embryo, while one of the two X chromosomes will be inactivated after the blastula stage (Lyon, Biol. Rev. 47: 1–35, 1972 ); now, it is known that there are several enzymatic genes on X chromosome, such as, glucose-6-phosphate dehydrogenase (G6PD) and hypoxanthine phosphoribosyl transferase (HPRT), so that the number of X chromosomes present in an embryo can be predicted by comparing strengths of activities of these enzymes. Although damage due to microscopic operation can be avoided during application of such enzymatic activity test on sexing of embryo, the survival rate of the embryo is low owing to the direct exposure of embryo in a reaction solution (Williams, Theriogenology 25:733–739, 1986),and furthermore, X-inactivation stages have not been verified among various species yet, which lead this method not being widely used.

Sex-determination of embryos by means of Y-specific nucleotides is based on two molecular biological principles: the first one comprising of using Y-specific DNA sequence as probe to hybridize genomic DNA extracts derived from the embryo; while the second one comprising of designing suitable primers based on Y-specific nucleotide sequences and carrying out in vitro amplification of gene sequence by means of PCR. Wherein, because of their high sensitivity, high accuracy and high efficiency, polymerase chain reaction method will become the most potentially practical technique among various methods.

In order to apply PCR on sex-determination of embryo of domestic animals, a nucleotide sequence specific against sex should be recognized at first, such as SRY one associated with testis determining factor (Sinclair el al., Nature 346:240–244, 990), certain Y-specific repetitive sequences (Nakahori et al., Nucleic Acid Res. 14:7569–7580, 1986), ZFX, ZFY genes homologous to X and Y chromosomes (zinc finger X chromosome, zinc finger Y chromosome) (Pollevick el al.,Bio/Technol. 10:805–807, 1989) and so on which are known to have sex-specific NUCLEOTIDE sequences. However, in those PCR-bassed sexing methods described above, each primer pair can recognize sex-specific gene fragments derived from only one sex chromosome whereas it can not detect simultaneously fragments derived from both of X and Y chromosomes so that an internal control primer derived from intrinsic gene must be added in the reaction. Since the existence of two groups of primer in the enzymatic amplification may readily result in competition therebetween and increase the probability of formation of primer dimer during in vitro amplification of gene, the simplicity of the method is greatly reduced consequently. Against this defect, the invention designs a group of primers homologous to both of X and Y chromosomes, which can amplify gene fragments of different lengths simultaneously from X chromosome and from Y chromosome, so that sex type of early cow embryo before implantation can be determined straightwardly from results of electrophoresis.

SUMMARY OF THE INVENTION

In order to promote practicability of application of PCR technology on sexing of cow embryo, primers used must be designed to be able to recognize at the same time both of nucleotide sequences of X and Y chromosomes, and, therefore , homologous ones located on X and Y chromosomes are the target genes to be searched by the invention. Heretofore, two groups of homologous genes have been recognized on sex hormosomes of mammal, namely: ZFX and ZFY genes (Aasen and Medrano, Bio/Technology 8:1279–1287, 1987), and amelogenin X gene and amelogenin Y gene (Leu et al.,Genomics 4: 162–168, 1989). Results of restriction map analysis showed that a restriction fragment length polymorphism (RELP) existed between ZFX and ZFY genes, while a length polymorphism existed between amelogenin gene X and Y. However, length variations can not obviously observed within cDNA sequences of cow amelogenin genes already known. With respect to this characteristic, it can be suggested that variation of sequence lengths is occurred within introns of bAML genomes. Results of a series of enzymatic cleavage on introns and comprehensive nucleic acid sequencings revealed that fifth introns derived from bAML genes of X and Y chromosomes have a length of 1684-bp and 1538-bp, respectively, and moreover, similarity of nucleotide sequences therebetween is only 45.1%.

Accordingly, the invention designs a pair of primers across a section of 126-bp nucleotide deletion in bAML gene intron5Y, such that PCR products having various lengths can be amplified against X and Y chromosomes respectively and thereby the object of sex determination can be achieved. After combining this method with a two stagewise enzymatic amplification, the bonding efficiency of this primer pair can be enhanced and the specificity of PCR products can be increased; thus, the sensitivity of sex determination can achieve an order of a single blastomere of cow embryo.

Accordingly, in its first aspect, the invention provides primer sets for using separately in enzymatic amplification of each of the first to the fifth intron in Holstein cow amelogenin gene, which primer sets are derived from 5' end and 3' end of each exon sequence in cow amelogenin cDNA sequence as well as from the 3'-untranslation region of such genes.

In a second aspect, the invention provides a oligonucleotide primer having a specific bonding ability to X sex chromosome and Y sex chromosome of Holstein cow embryonic cell. In particular, the invention provides a oligonucleotide primer which can bind specifically to the fifth intron sequence of amelogenin gene located on the X sex chromosome and Y sex chromosome of Holstein cow embryonic cell.

In a third aspect, the invention provides a primer pair having a oligonucleotide sequence selected from the group consisting of fragments of the fifth intron sequence in amelogenin gene located on Holstein cow sex chromosomes (bAMLX INTRON 5X and bAMLY INTRON 5Y) and those having a homology of higher than 60% with any fragment of such gene sequences, wherein said gene sequences have been deposited respectively in Gene Bank, Genome Sequence Data Base National Center for Genome Resources, USA, with accession number as L48608 for bAMLX INTRON 5X gene sequence and as L48609 for bAMLY INTRON 5Y, respectively.

In a fourth aspect, the invention provides a primer pair having an ability to bind at same time to sequences of intron 5X and intron 5Y of bAML gene as well a being usable as upstream sexing primer (pbAMLX5XY(+)) and as downstream sexing primer (pbAMLX5XY(-)) in cow embryo sexing PCR, wherein nucleotide sequences of such primer pair are selected from group consisting of:

pbAML5XY(+): 5'-AAATTCTCTCACAGTCCAAG-3' (SEQ ID NO:1)

pbAML5XY(-): 5'-CAACAGGTAATTTTCCTTTAG-3' (SEQ ID NO:2) and those having a homology of higher than 70% with the nucleotide sequences thereof.

In a fifth aspect, the invention provides a process of cow embryo sexing by means of enzymatic amplification through PCR, comprise steps of: placing cow embryo in a low tonic solution and under heating condition to denature its proteins and expose its template DNA; carrying out two-stagewise PCR reaction by using primer set above-mentioned; containing PCR products; electrophoretic separation; and observing under UV light, wherein, PCR product derived from X chromosome has a length of 467-bp, while PCR products derived from Y chromosome have lengths of 467-bp and 341-bp, thereby sex type of the cow embryo can be readily determined.

In a sixth aspect, the invention provides use of above-mentioned primer pairs or primer sets in sexing of cow embryo.

In a seventh aspect, the invention provides a kit for sexing cow embryo, comprising above-mentioned primer pairs or primer sets, DNA Taq polymerase, dNTP and source of magnesium ion.

The above and other aspects, as well as advantages and features of the invention will be illustrated further in detail in the following description and examples with reference to accompanied drawings in which:

FIG. 3 shows the relative information of L48608 (for bAMLX intron 5X gene sequence) and L48609 (for bAMLY intron5Y gene sequence).

Figure 4:
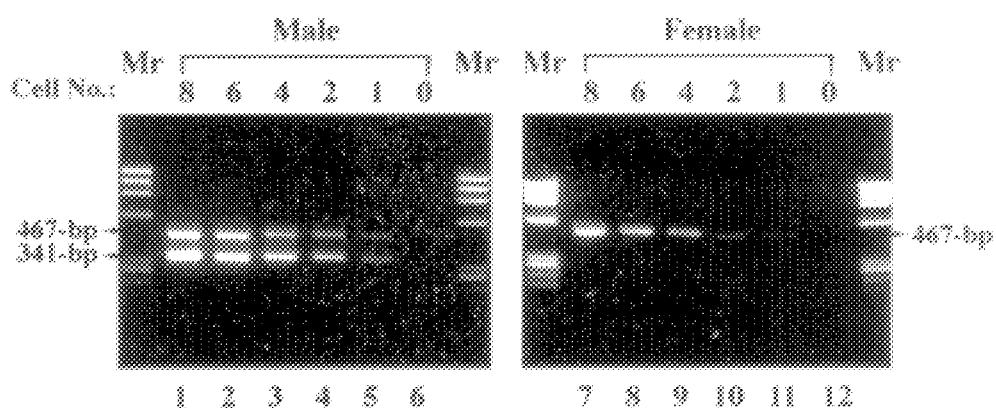

FIG. 4 shows a process for determining sensitivity of sexing by using a X-Y homologous sex primer pair pbAML5XY(+) and pbAML5XY(-). After a series of dilution of leucocytes obtained from male and female cows, draw different number of cells (8-, 6-, 4-, 2-, and 1-cell) under high amplification microscope and use them as template in PCR enzymatic amplification to yield the indicated results. M: molecular weight index of φ×174/HaeIII.

Figure 5:
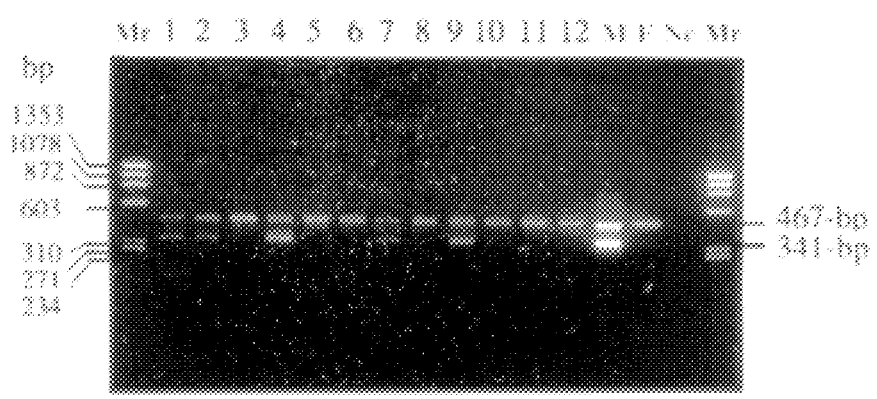

FIG. 5 shows the result of sex determination on a single blastomere derived from blastula stage. ♂ and ♀ represent leucocytes as control samples derived from male or female cows, the male (♂) cell yields PCR products having 467- and 341-bp, while female (♀) cell results in a single fragment of 467-bp as PCR product, results show that sample No. 1, 2, 4, 7 and 9 are male embryos, and sample No. 3, 5, 6, 8, 10, 11 and 12 are all determined as female embryos.

FIG. 6 shows the nucleotide sequence of the intron 5 in Holstein cow bAML X gene. The length thereof is 1684-bp with a nucleotide composition of 542 adenine (A), 265 cytosine(C), 327 guanine (G) and 550 thymine (T).

FIG. 7 shows the nucleotide sequence of the intron 5 in Holstein cow bAML Y gene.

The length thereof is 1539-bp with a nucleotide composition of 544 adenine (A), 216 cytosine(C), 245 guanine (G) and 534 thymine (T).

Figure 8:
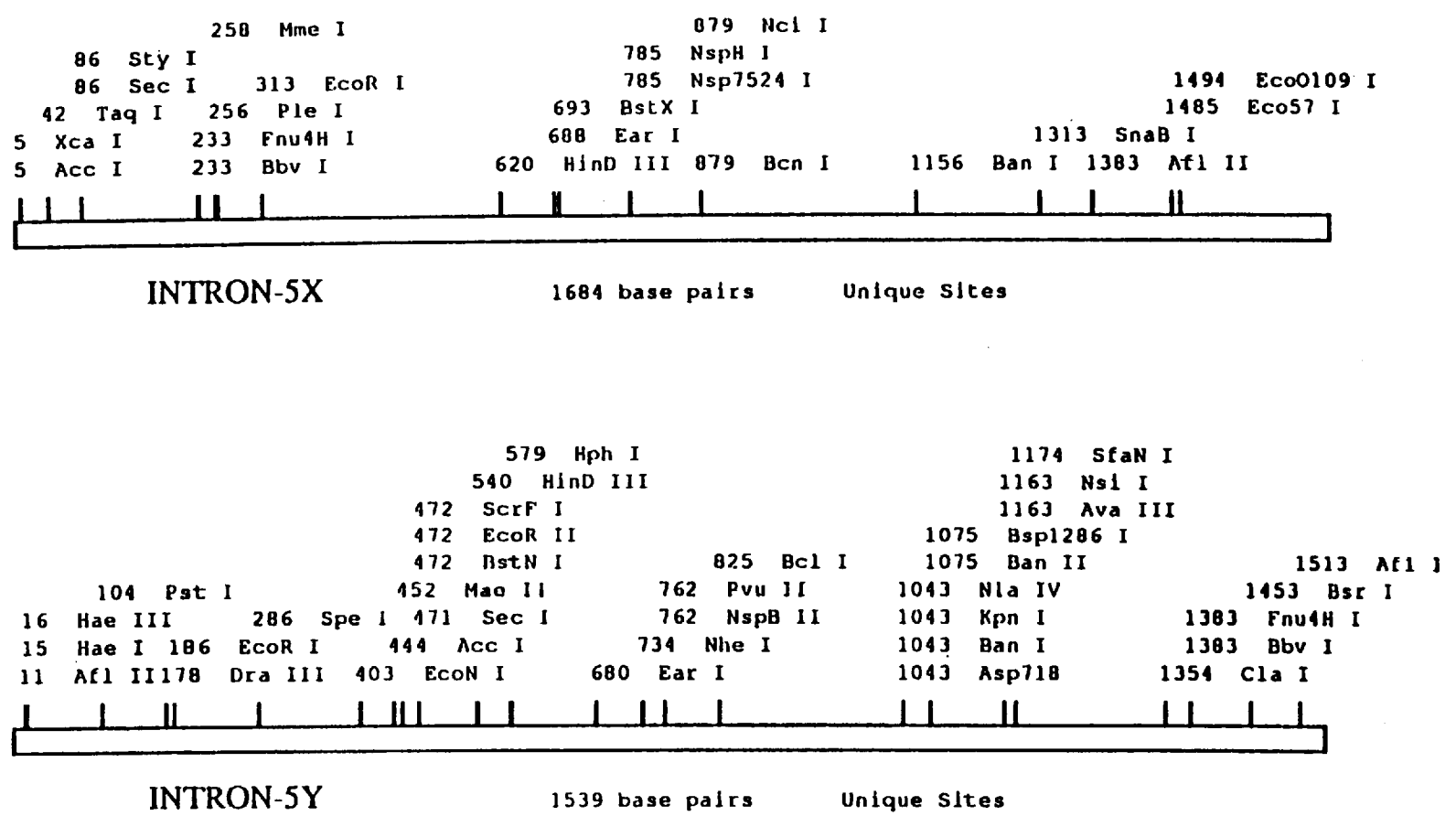

FIG. 8 shows the restriction map derived from unique enzyme cutting size of intron5X and intron5Y in Holstein cow bAML gene. The vertical solid line indicates the relative position acted by restriction enzyme; numbers indicates positions in the nucleotide sequence recognized by the restriction enzyme.

Figure 9:
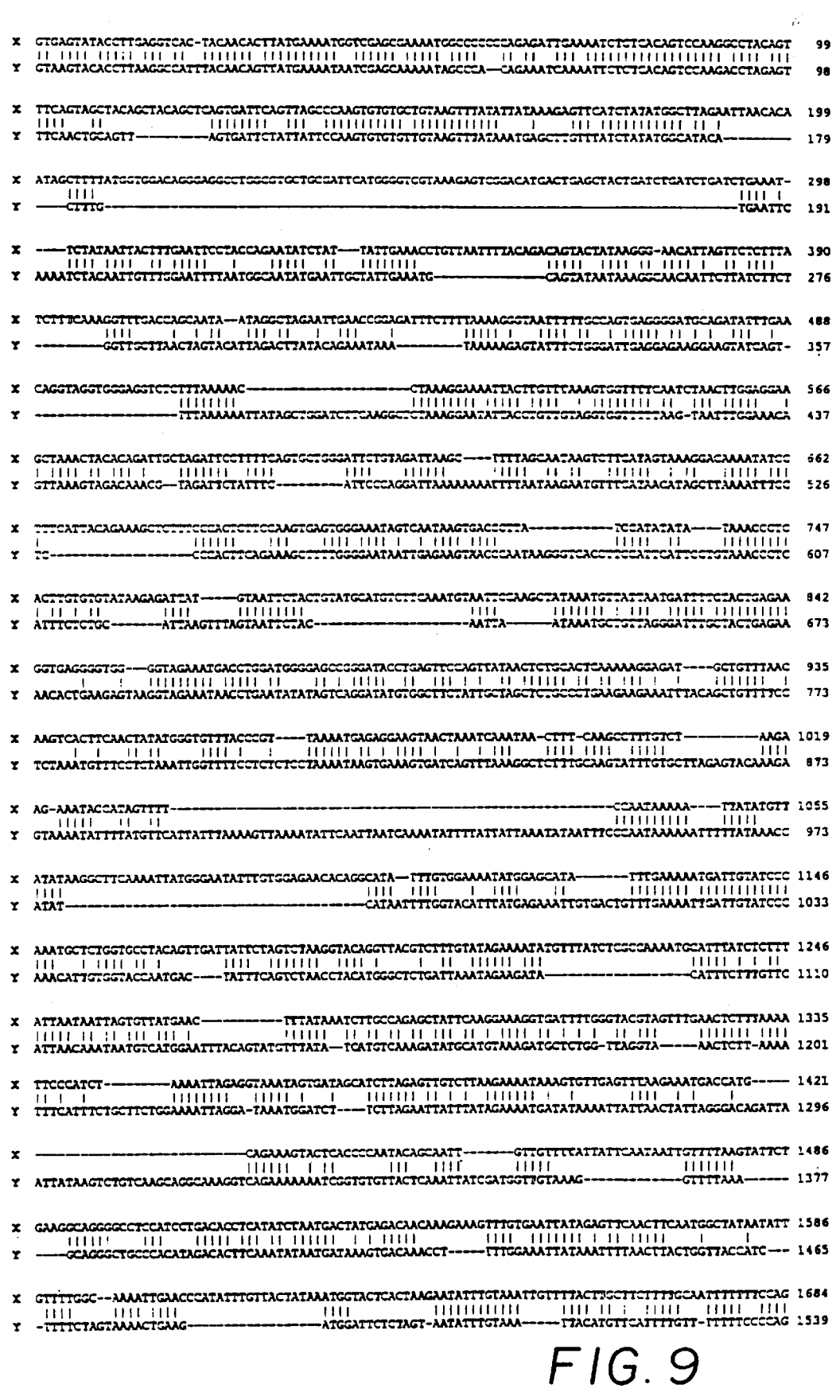

FIG. 9 shows the comparison of intron 5 sequences between Holstein cow bAML X and Y genes. Vertical solid line indicates coincidental sequences between intron5X and intron5Y, while horizontal dot line indicates deletions in nucleotide sequence; the results from comparison reveals a homology of only 45.1% between intron5X and intron5Y sequences.

FIG. 10 shows a group of primers for sexing cow embryo by using intron5 sequence in Holstein cow bAML X and Y gene as template. The upstream sexing primer locates on a position of 71th to 90th nucleotide in bAML intron5X, while the downstream sexing primer locates on a position of 537th to 517th nucleotide in bAML intron5X.

Figure 11:
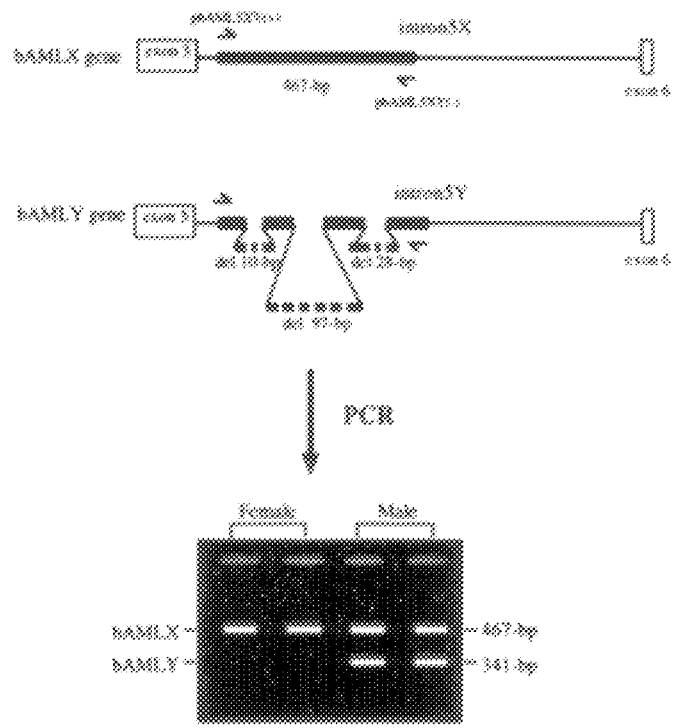

FIG. 11 shows the bonding position of pbAML5XY(+) and pbAML5XY(−) sexing primers on cow bAML gene and the lengths of PCR products thereof. A gene fragment of 467-bp as PCR product is to be produced through bonding of this primer pair on intron5X sequence, whereas a gene fragment of 341-bp as PCR product is to be produced through bonding on intron5Y sequence.

Figure 12:
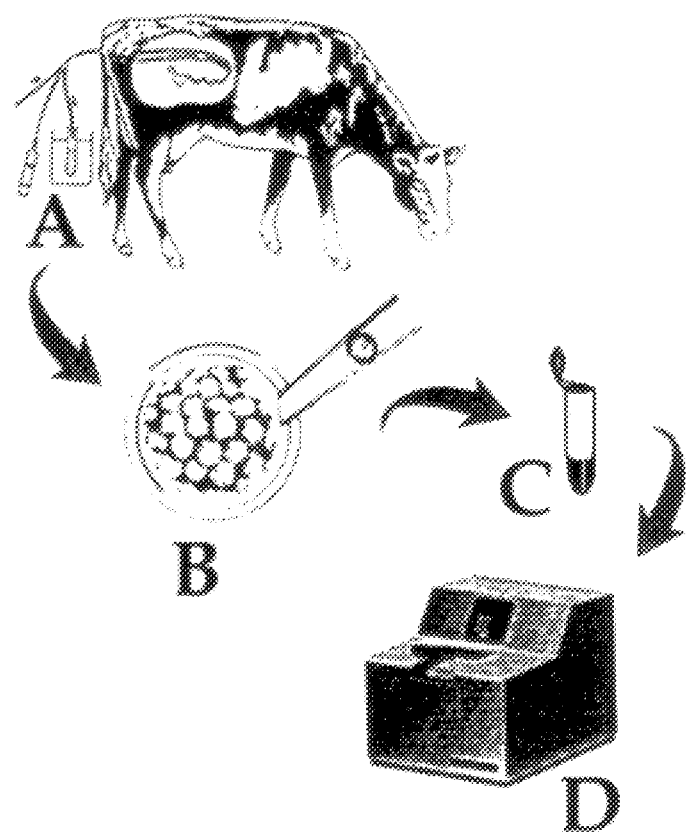

FIG. 12 shows a brief flowsheet of sexing cow embryo. (A) Collect un-implanted morula or blastula via non-surgical method; (B) Pluck single blastomere under microscope at high amplification; (C) Placing the single blastomere in a 0.5-ml microcentrifuge tube, and carry out PCR sexing in thermocycler.

DETAILED DESCRIPTION OF THE INVENTION

1. Detection of sex-specificity of Holstein cow amelogenin gene

According to Nakahori et al. (Am. J. Med. Genet. 39:472–473, 1991), human X and Y sex chromosomes bear an amelogenin (hAMLX) and an amelogenin-like (hAMLY) gene sequences respectively, and although a homology of higher than 90% exists therebetween, the intron 3 in hAMLX sequence of X chromosome has an additional sequence of 177-bp than that in hAMLY sequence so that proper primers designed based on these two gene sequences will be extremely suitable for using as sex-determining indices for human embryo and criminal trial. Now, it is known that Holstein cow X and Y chromosomes bear also AMLX and AMLY gene sequences, respectively. However, it has not been clear whether sex-specific length variation exists between bovine bAMLX and bAMLY gene sequences as the case in human being.

Accordingly, the invention employed at first the Southern bloty hybridization analysis to demonstrate that Holstein cow amelogenin gene sequence has a restriction map polymorphism and this result had opened a possibility for creacting a novel primer useful for sexing cow embryo.

DNA samples used in the Southern blot hybridization analysis were obtained from Holstein cows bred in Agricultural Pilot Farmer of National Taiwan University, Taiwan, ROC, wherein, parts of ear tissues of several male and female cows were scissored and then were subject to DNA extraction. Genomic DNA samples thus obtained from male and female cows were cleaved by various restriction enzymes, electrophoretically separated on 0.8% agarose gel, and subsequently transferred and immobilized those DNA fragments thus colloidally moved apart on a nitrocellulose membrane according to a standard practice as described by Sambrook el al.(Molecular Cloning, Cold Spring Harbor Lab. Press, pp 914–959, 1989.)

The probe used in the hybridization is a nucleic acid sequence synthesized by in vitro enzymatic amplification method based on the amelogenin gene cDNA sequence reported by Shimokawa et al. (J. Biol. Chem. 262: 4042–4047, 1987), and comprises a gene fragment of exon5 in AML gene.

Figure 1:
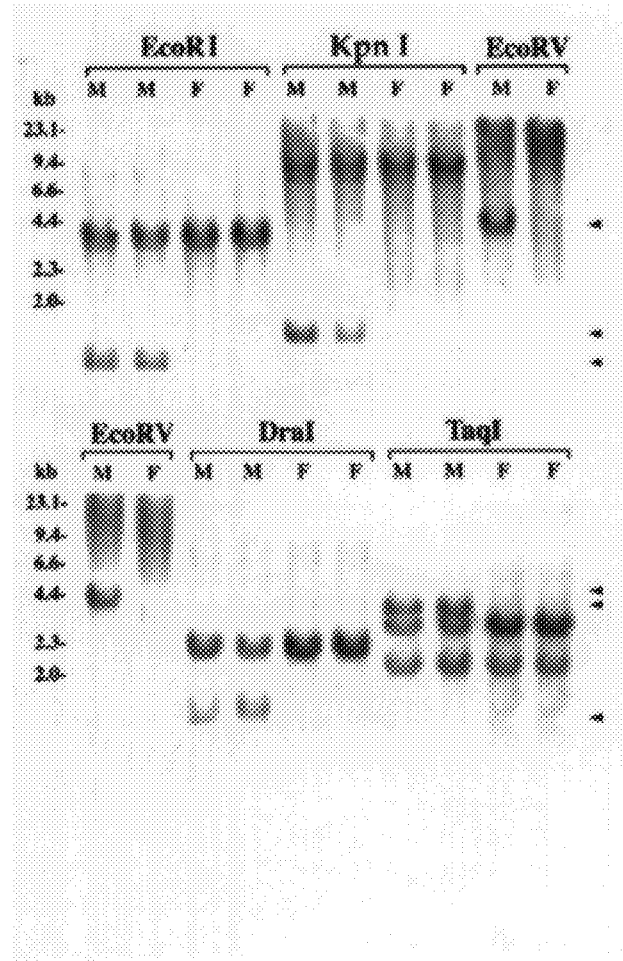
FIG. 1 shows the results of the Southern blot hybridization analysis by using as probes fragments of exon5 of bAML gene obtained by cleaving amelogenin genes of male and female cow genomes with restriction enzymes EcoRI, KpnI, EcoRV, DraI, and TaqI. That indicated by the arrow is a Y-specific gene fragment.

As shown in FIG. 1, the result of the Southern blot hybridization analysis which involves cleavage by 5 restriction enzymes, i.e., EcoRI, KpnI, EcoRV, DraI and TaqI, reveals that a significant difference does exist between male and female cow amelogenin gene fragments, i.e., all amelogenin genes from male cows have an additional hybridization fragment than those from female cows and their lengths are: EcoRl, 1.2-kb; KpnI, 1.5-kb; EcoRV, 4.4-kb; DraI, 1.4-kb; and, 3.8-kb, respectively. Such an additional hybridization signal is just the one presented by the sex-specific sequence in bAMLY gene located on Y chromosome. However, since bAMLX and bAMLY cDNAs is highly similarity such that there are only 41 different nucleotides between their coding regions (Gibson el al., Biochem. 31:8384–8388, 1992), the above-mentioned difference between bAMLX and bAMLY gene sequences must occur in intron sequences of cow amelogenin gene. In order to prove this suggestion, the invention conducted further an in vitro amplification to reproduce sequences of all the introns in the amelogenin gene and compared sequences between corresponding introns located on bAMLX and bAMLY genes.

The Holstein cow amelogenin gene has a total of 5 intron sequences. On base of the cow amelogenin cDNA sequence established by Gibson et al. (Biochem. 30:1075–1079, 1991), primers can be designed from 5'-end and 3'-end of each exons and from the 3'-untranslation region of that gene and can be used in enzymatic amplification for reproducing the first to the fifth intron. Those primers are listed in Table 1.

TABLE 1

Oligonucleotide sequences used in amplification of each intron sequence in bovine amelogenin gene.

| amplified region | primer designation | oligonucloetide sequences | Tm (°C.) |
|---|---|---|---|
| Intron 1 | | | |
| (+) | bE1(+) | 5'-CACTGAGAACGTGTGTTC-3' | 54 (SEQ ID NO: 3) |
| (−) | bE2(−) | 5'-AGGAGGCAGGCAAACAAAA-3' | 56 (SEQ ID NO: 4) |
| Intron 2 | | | |
| (+) | bE2(+) | 5'-ATTTTGTTTGCCTGCCTCCT-3' | 58 (SEQ ID NO: 5) |
| (−) | bE3(−) | 5'-AGTTGATATAACCAGGGTGC-3' | 58 (SEQ ID NO: 6) |
| Intron 3 | | | |
| (+) | bE3(+) | 5'-GCACCCTGGTTATATCAACT-3' | 58 (SEQ ID NO: 7) |
| (−) | bE4(−) | 5'-GTCTTATCATGCTCTGGTAC-3' | 58 (SEQ ID NO: 8) |

TABLE 1-continued

Oligonucleotide sequences used in amplification of each intron sequence in bovine amelogenin gene.

| amplified region | primer designation | oligonucloetide sequences | Tm (°C.) | |
|---|---|---|---|---|
| Intron 4 | | | | |
| (+) | bE4(+) | 5'-GTACCAGAGCATGATAAGAC-3' | 58 | (SEQ ID NO: 9) |
| (−) | bE5(−) | 5'-TCGTAACCATAGGAAGGG-3' | 54 | (SEQ ID NO: 10) |
| Intron 5X | | | | |
| (+) | bE5(+) | 5'-AGCAACAGACAAGACCAAG-3' | 56 | (SEQ ID NO: 11) |
| (−) | bE6(−) | 5'-TTTACTTCAGGTCTCTTCTC-3' | 56 | (SEQ ID NO: 12) |
| Intron 5Y | | | | |
| (+) | bE5(+) | 5'-AGCAACAGACAAGACCAAG-3' | 56 | (SEQ ID NO: 13) |
| (−) | bE6Y(−) | 5'-GTAGAATGATTATGGGCACAAA-3' | 60 | (SEQ ID NO: 14) |

Figure 2:
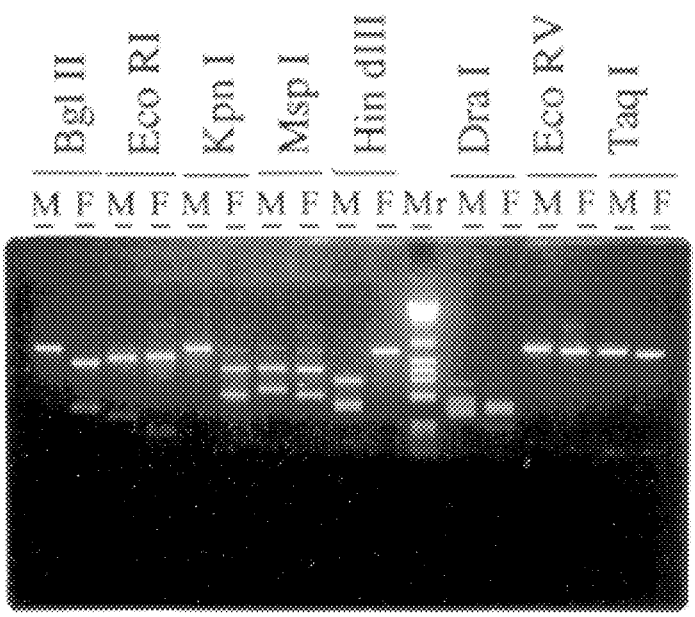
FIG. 2 shows the restriction map of the intron 5 in bAML gene of male and female Holstein cows. All of the seven enzymes shown in the map, i.e., BglII, EcoRI, KpnI, MspI, HindIII, DraI, EcoRV, and TaqI, can distinguish male fragments from female one.

Results obtained through amplifying each intron sequence of bAML genes located on male and female cow genomic DNAs show that lengths of intron, 1, 2, 3 and 4 are 1.35-kb, 2.6-kb, 1.4-kb and 0.4-kb, respectively; however, after cleaving with above-mentioned 5 restriction enzymes, the first to the fourth intron sequences show little differences between bAMLX and bAMLY genes. Noteworthily, when the fifth exon sequence homologous to both bAMLX and bAMLY genes is used as upstream primer in combination with 3'-untranslational region of bAMLY gene as downstream primer (Table 1) in PCR amplification, an intron5Y fragment of 1.7-kb is obtained. Such fragment is shorter than the intron5X fragment (1.8-kb) obtained through amplifying from bAMLX gene, and meanwhile, after being cleaved with various restriction enzymes, i.e., BglII, DraI, EcoRl, EcoRV, HindIII, KpnI, MspI and TaqI, a sex-specificity is shown between intron5X and intron5Y with respect to above-mentioned specific restriction enzymes, such as shown in FIG. 2. As the result of analysis of such researches, it is evident that certain sex-specific restriction sites must occur in the intron5 sequence of cow amelogenin genes.

2. Nucleic acid sequencing and homology comparison of intron5 sequences between bAMLX and bAMLY genes In order to find out the sex-specific sequence in bovine amelogenin gene such that suitable primers can be designed for subsequently sexing of cow embryo, the present inventors had cloned the above-mentioned intron5X and intron5Y in a plasmid pGEM-7zf(+), respectively, by means of a DNA blunting ligation kit (Takara, Japan), and subsequently carried out sequencing and comparison by employing a DNA automatic sequencing system. The sequencing process is as described as following:

(1) Proceeding of sequencing reaction: the plasmid used in sequencing is obtained through purification by means of Wizard# Miniprep DNA purification system (Promega, USA) and, after determining its concentration and purity by $OD_{260}/OD_{280}$, it is subject to a fluorescent labeling reaction by using Taq DyeDeoxy# Terminator Cycle Sequencing Kit (Applied Biosystem Inc., USA),in which the reaction content consists of: 1 μg of plasmid DNA having good purity, 3.2 pmol of primer for sequencing, and 9.5 μl of reaction premix (Terminator Ammonium Cycle Sequencing, ACS premix) with a composition of: 4 μl of 5× TACS buffer (1× TACS buffer=80 mM Tris-HCl, 2 mM $MgCl_2$, 20 mM $(NH_4)_2SO_4$, pH 9.0), 1 μl dNTP mixture (37.5 μM dITP, 7.5 μM dATP, 7.5 μM dTTP, and 7.5 μM dCTP), and 1 μl of each of G, A, T, C Dye Deoxy Terminator, as well as 0.5 μl of AmpliTaq DNA polymerase (8 U/μl), with a final volume of 20 μl, and eventually, two drops of mineral oil overlaying the reaction mixture. Then, the reaction mixture is transferred in a 0.5 μl thin wall centrifuge tube, and subject to cycle reaction in a MJ Research PTC-100 thermocycler as follows preheating the thermocycler to a temperature of 96° C. prior to placing the centrifuge tube therein and thereafter, carrying out 23 heating cycles as follow: 96° C., 30 sec; 50° C., 20 sec; 60° C., 4 min; following by reducing quickly the temperature down to 4° C. and maintaining at this temperature till the final extraction step.

(2) Purification of sequencing products: to 20 μl of the reaction mixture obtained after completion of the reaction described above, 80 μl of double distilled water is added to extend the volume to 100 μl , and remove the mineral oil overlaid on the reaction mixture by extraction with equal volume of chloroform/isoamyl alcohol mixture and then once with equal volume of phenol/ $ddH_2O/CHCl_3$ (68:18:14) mixture; precipitate reaction products by adding 0.1 X volume of 3M NaOAc solution and 250–300 μl absolute alcohol, collect DNA pellets particles by centrifuge, wash once with 70% alcohol, and after removing residual alcohol and moisture in the pellets by means of a vacuum concentration apparatus (Savant, USA), fine particles thus obtained can be stored at −20° C. or subject to electrophoresis immediately.

(3) Preparation of eletrophoretic gel used in sequencing: the electrophoretic gel used in sequencing is prepared according a partial modified method with respect to the instruction of 373A DNA Sequencing System User's Mannual (1993), comprises steps of: adding 40 g urea in 9.5 ml of acrylamide/bisacrylamide (19:1) and 16 ml of 5×TBE buffer and heating under slight stirring to complete dissolving of urea, filtering and adding $ddH_2O$ to adjust its volume to 80 ml, ; after cooling the solution, adding 400 μl of fresh 10% ammonium persulfate (APS) and 45 μl of TEMED (N,N,N',N'-tetramethyl ethylenediamine), and after mixing homogeneously by slight shaking, pouring the solution into the space between two pieces of special glass plates edge-sealed with tape, following by standing horizontally for 2 hours allowing complete gelling, thereby giving polyacrylamide gel of 0.4 mm thick useful for sequencing.

(4) After dissolving in 3–4 μl of a fresh loading buffer (deionized formamide: 50 mM EDTA=5:1), dried sequencing products obtained above were subject to electrophoretic separation on a ABI DNA automatic sequencer (Applied Biosystem Inc., USA) under conditions based on set values of that 373A electrophoresis apparatus: 2500 volt/40 mAmp/ 40 Watt, for 7 hours, and data obtained throughout the electrophoresis were collected (Data collection, version 1.2.1), analyzed immediately (Data Analysis, version 1.2.1), and finally, stored sequencing results for reading later by a computer.

Results from nucleic acid sequencing indicate that intron5X in bAMLX gene has an actual sequence length of 1684-bp, and a nucleotide composition of 542 adenine (A), 265 cytosine (C), 327 quanine (G) and 550 thymine (T), as shown in FIG. 6 whereas intron5Y in bAMLY gene has an actual sequence length of only 1539-bp, and a nucleotide composition of 544 adenine, 216 cytosine, 245 quanine and 534 thymine, as shown in FIG. 7. Both of these two gene sequence have been deposited in GeneBank; Genome Sequence Data Base, National Center for Genome Resources, USA, and designated by the system for these two novel genes accession numbers as L48608 (for bAMLX intron 5X gene sequence) and L48609 (for bAMLY intron5Y gene sequence), respectively, of which the relative information are given in FIG. 3.

In order to confirm further the sex-specificity of intron5 in bAML genes, a Southern blot hybridization analysis was carried out against male and female Holstein cow genomic DNA sequences by using intact intron5Y sequence as probes. Results had shown that, under stringent hybridizataion conditions, the intron5Y probe was permitted only to hybridize with male cow genomic DNA, which indicated that an extremely great difference must exist between intron5X and intron5Y nucleic acid sequences. Indeed, the unique size of restriction map of these two intron sequences had revealed relatively great diversity (FIG. 8).

Under comprehensively comparison of necleic acid sequences through a DNASTAR nucleic acid analysis computer software (Dnastar Inc.,Madison, Wis., USA), it became more evidently that the homology between these two intron sequences was relatively low (FIG. 9), as the similarity therebetween was only 45.1%.

This was quite contrary to that of human amelogenin gene, since, according to Nakahori et al. (Am. J. Med. Genet. 39:472–473, 1991), the similarity of intron5 sequences between human bAMLX and bAMLY genes may be up to 86.4%, and the similarity of exon sequences therebetween is even as high as 93%. Undoubtedly, intron5X and intron5Y sequences of bAML gene are the most preferable candidates for using in cow sexing by applying PCR technique.

3. Designing of primers useful in cow embryo sexing:

Regarding cow embryo sexing through employing Y-specific primers described in prior art heretofore, primers used were those that comprised only haploid SRY gene or several Y-specific repetitive sequences; those prior art tests had to use a group of non-sex-specific primers as internal control during PCR sexing of cow embryos so that, based on fragments of the internal control amplified, the un-amplification of Y-specific fragments could be attributed to the fact that the cow is a female one and not to failure of PCR reaction (Ustumi et al., Theriogenology 41:323, 1994; MacHaty el al., J. Reprod. Fert. 98:467–470, 1993). In view of this, the invention is directed specifically design a group of primers based on the intron5 sequence of bAML gene, which primers can bond on both of intron5X and intron5Y sequences simultaneously such that both male and female embryonic cells can give enzymatic amplification , thereby eliminates the interference involved in the incorporation of additional internal control.

Through comprehensive comparison of intron5X and intron5Y sequences in bAML gene (FIG. 9), it can be seen that, with respect to intron5X, intron5Y comprises from position of its 179th nucleotide to that of its 185th nucleotide an distict nucleotide deletion having a length up to 97-bp, and further, on the upstream and downstream sides of that deletion, also presented the several short deletions. A pair of sexing primers were designed according to this deletion region. The upstream sexing primer, pbAML5XY(+), is on a position comprising 71th to 90th nucleotide in bAML intron 5X, while its corresponding position in intron 5Y comprises a position between 70-nt and 89-nt. The downstream sexing primer, pbAML5XY(-), is on a position comprising 537th to 517th nucleotide in bAML intron5X, while its corresponding position in intron5Y comprises a position between 409-nt and 389-nt (FIG. 10). Oligonucleotide sequences of those primers are shown in following:

(A) Designing of upstream sexing primer:

```
                        71-nt                  90-nt
bAML intron 5X:   5'-AAAATCTCTCACAGTCCAAG-3'
                                              (SEQ ID NO: 15)

pbAML5XY(+):      5'-AAATTCTCTCACAGTCCAAG-3'
                        _
                                              (SEQ ID NO: 16)

70-nt                  89-nt
bAML intron 5Y:   5'-AAATTCTCTCACAGTCCAAG-3'
                                              (SEQ ID NO: 17)
```

(B) Designing of downstream sexing primer:

```
                        537-nt                 517-nt
bAML intron 5X:   5'-AAACAAGTAATTTTCCTTTAG-3'
                                              (SEQ ID NO: 18)

pbAML5XY(-):      5'-CAACAGGTAATTTTCCTTTAG-3'
                       _    __   _
                                              (SEQ ID NO: 19)

409-nt                 389-nt
bAML intron5Y:    5'-CAACAGGTAATATTCCTTTAG-3'
                                              (SEQ ID NO: 20)
```

Oligonucleotide primers were synthesized by Quality Systems Inc., Taipei, Taiwan on an Applied Biosystems 391 DNA synthesizer through solid state coupling of triesters. Deprotection and cleavage from solid state were carried out with 28% ammonia. Purification of crude oligonucleotide mixture was performed according to the method described by McBridge et al. (Biotechniques 6:362–367,1988). Thereafter, the desired synthetic primers were separated by column chromatography on an oligonucleotide purification column(OPC column, Applied Biosystems Inc., USA)

The upstream sexing primer (pbAML5XY(+)) comprises 20 oligonucleotides, a molecular weight of 6125 g/mole, a G+C content of 40%, Tm value of 56° C., and other relative characteristics and analytical values as shown in Table 2. The design of the upstream primer sequence can match completely coincidental to template sequence of AML intron5Y, whereas the primer has a mismatch base against the template sequence of intron5X at the fourth nucleotide on its 5' end ($A_4 \rightarrow T_4$).Since this mismatch nucleotide is on the 5' end of the adjacent primer so that it has little influence on the bonding efficiency of that primer on the intron5X sequence of bAML gene. In general, the principle of PCR sexing is based on whether Y chromosome-specific gene fragments are present or not. One of the advantages of the design of the primer according to the invention is that its bonding specificity against Y chromosome gene fragments is higher than that against X chromosome gene fragments so that the sexing ability against Y chromosome can be increased while the error probability of cow embryo PCR sexing can be eliminated consequently. The same designing concept applies on the downstream sexing primer (pbAML5XY(-)) wherein its first and sixth base are mismatched against the template sequence of intron5X in bAML gene ($A_1 \rightarrow C_1; A_6 \rightarrow G_6$) and its 12th base is mismatched against intron5Y template sequence ($A_{12} \rightarrow T_{12}$). The associated characteristics and analytical values of this primer are also shown in Table 2.

TABLE 2

Basic information of olgonucleotide primers used in cow embryo sexing.

| primer-pair | pbAML5XY(+) | pbAML5XY(-) |
|---|---|---|
| Nucleotide length | 20 mer | 21 mer |
| Molecular weight | 6125 g/mol | 6475.3 g/mol |
| Tm thermodynamic | 55.1° C. | 56.8° C. |
| Filter Tm | 47.5° C. | 49.2° C. |
| % GC Tm | 64.2° C. | 63.0° C. |
| AT + GC Tm | 56.0° C. | 56.0° C. |
| Absorbance | 5.1 nmol/A260 | 4.9 nmol/A260 |
| Percent GC | 40% | 33.3% |
| Delta G | −28.3 kcal/mol | −30.6 kcal/mol |
| Delta H | −140 kcal/mol | −159 kcal/mol |
| Delta S | −367.8 eu | −426.0 eu |
| 3' end Delta G | −6.4 kcal/mol | −6.0 kcal/mol |
| No. of base runs | 0 | 1 |
| No. of palindromes | 0 | 0 |
| No. of hairpin loops | 0 | 2 |

When used in PCR sexing of cow embryos, this primer pair can bind on both of intron5X and intron5Y sequences in bAML gene, and the PCR product derived from X chromosome has a length of 467-bp, while those derived from Y chromosome has a length of 341-bp, with a difference in length of 126 base pairs therebetween so that cow sex can be readily distinguished by electrophoretic separation on 2% agarose gel.

4. Process for applying pbAML5XY(+) and pbAML5XY(-) primer pair in cow embryo sexing Because the amount of DNA template occurred during PCR sexing of cow embryos is relatively small, comprising merely a haploidal X and Y chromosome in a diploid chromosome from only a single blastomere, allowing not any operational error, therefore, when carrying out PCR reaction, template DNAs of high purity can not obtained by means of conventional DNA extraction. In order to sex successfully every cow embryonic cell, a single intact blastomere is placed directly in a PCR reaction microcentrifuge tube of 0.5-ml thin wall type and frozen immediately in a 70° C. refrigerator until used in PCR sexing. Such a single blastomere is obtained from morula or blastula on the sixth or seventh day after conception under a phase contrast microscope at 400× amplification by puncturing zone pellucida with ultra fine glass needle, drawing one blastomere therein and placing directly on the bottom of a microcentrifuge tube (FIG. 12).

Regarding PCR sexing, 20 μl of deionized sterile water (ddH$_2$O) was added at first to the single blastomere in the microcentrifuge tube, and overlaid with 50 μl light mineral oil (Sigma), then, placed in a PCR thermocycling reactor (MT-100, MJ Res,. USA) and heated at a temperature of 97° C. for 5 minutes to carry out the pretreatment of protein denaturation. Whereupon, in low tonic solution and under heating condition, cell content of the blastomere such as cytoplasmic membrane, nuclear membrane and DNA binding protein of the blastomere will be burst and/or denatured and accompanied with DNA exposure, and part of chromosomes were partial denatured and exhibited single stranded unwinding DNA structures. In order to keep the stability of the denaturation, immediately after completion of the preheating treatment, it was cooled to 4° C., or quickly cooled by placing directly in a ice bath.

During pretreating of the blastomere, a PCR reaction buffer was prepared according to the composition shown in Table 3. When the temperature of the microcentrifuge tube treated was lowered to 4° C., 30 μl of PCR reaction buffer was added and carried out enzymatic amplification at a total volume of PCR reaction mixture of 50 μl. The composition of the PCR reaction buffer had been adjusted elaborately in order to optimize the amplification effect of PCR reaction on a single cell, and hence, concentrations of its components differed somewhat with respect to those used in conventional standard PCR reaction (Mullis and Faloona, Meth. Enzymo. 155:335–350, 1987) wherein: for 2 mM Mg$^{2+}$, MgSO$_4$ was used in replace of traditional MgCl$_2$; concentration of primer was increased from prior art 0.1 μM to 0.4 μM so as to increase the probability of binding to the sparse template DNA; and also the amount of thermostable Taq DNA polymerase (Premega, USA) added (2.5 U) was twice that in traditional PCR (1.25 U) (Table 3), so that a maximum efficiency of nucleic acid synthesis can be achieved.

TABLE 3

Composition of PCR reaction buffer used in cow embryo sexing

| component | concentration |
|---|---|
| 1X PCR buffer | |
| Tris-HCl (pH 8.8) | 20 mM |
| (NH4)2SO4 | 10 mM |
| KCl | 10 mM |
| MgSO4 | 2 mM |
| Triton X-100 | 0.1% |
| BSA | 0.1 mg/ml |
| dNTPs | |
| dATP | 200 μM |
| dCTP | 200 μM |
| dGTP | 200 μM |
| dTTP | 200 μM |
| Primers | |
| pbAML5XY(+) | 0.4 μM |
| pbAML5XY(-) | 0.4 μM |
| Template | |
| blastomere | 1-cell |
| Taq DNA polymerase | 2.5 Unit |

PCR reaction conditions for cow embryo sexing adopted two-stagewise heating cycle. The design of heating cycle used in the first stage was aimed at increasing the binding efficiency of the primer on the template DNA and, accordingly, the annealing temperature was set at 53° C. (Tm −3° C.), and, after 20 cycles of heating cycle, proceeded into the second stage. The design of this second stage was focused on the amplification of gene fragments and the specificity of PCR reaction products. Consequently, the annealing temperature was raised to 54° C. (Tm −2° C.), and carried out 30 heating cycles.

Each reaction step of the heating cycles was accomplished within a predetermined constant time period, e.g., time for denaturing of template DNA (94° C.) was 30 seconds, that for annealing (53° C. or 54° C.) was one minute, and that for elongation of nucleic acid sequence (72° C.) was also one minute. After completion of the two-stagewise heating cycle, a sustaining extending of nucleic acid sequence (72° C.) was carried out over 5 minutes to assure amplification of every gene fragment to be sufficiently accomplished ; and finally, terminated at 4° C. for 2 minutes so that the whole process was completed as shown in Table 4.

TABLE 4

Conditions used in two-stagewise PCR reaction.

Pretreatment: protein denaturation and template DNA exprosure of embryonic blastomere 1. 97° C., 5 min
2. 4° C., 3 min The first stage: enhancing the efficiency of annealing 1. denaturation of template DNA: 94° C., 30 sec
2. annealing of primers: 53° C., 1 min
3. extending of nucleic acid sequence: 72° C., 1 min
4. repeat 20 cycles The second stage: enhancing amplification of gene fragment and specificity of products thereof 5. denaturation of template DNA: 94° C., 30 sec
6. annealing of primers: 54° C., 1 min
7. nucleic acid sequence extending: 72° C., 1 min
8. repeat 30 cycles
9. sustaining amplification of nucleic acid: 72° C., 5 min
10. termination: 4° C., 2 min Once the PCR reaction was complete, added 1 ul of staining indicator (6X dye; 0.05% bromophenoblue, 50% glycerol) into 10 ul of PCR product and sufficiently mixed. Then, loaded the mixture on 2% high transparent agarose gel (0.5% agarose gel, 0.75% sygner gel, 0.1 mg/ml ethidium bromide) and performed mini gel electrophoresis (100 voltage, 20 min). Thereafter, observed under ultraviolet light and recorded results by photography on Polaroid 667 film. The time taken from obtaining of the single blastomere to completion of PCR sexing was only 4 hours so that time required for in vitro cultivation of cow embryo could be reduced, thereby surviability of the embryo re-implantated in the cow body after sexing might be increased.

EXAMPLE 1

Employing leucocytes of male and female Holstein cows to test the identificability and sensitivity of primer pair of pbAML5XY(+) and pbAML5XY(-)

In order to understand the accuracy of the primer pair according to the invention in sexing, cervical bood samples were sampled from 15 female and 6 male Holstein cows bred in the farm of the National Taiwan University, Taipei, Taiwan, and separated leucocytes therein by Ficoll-Paque Plus method (Pharmacia Biotech, USA). The detailed procedure of leucocyte separation was as following: centrifuge 10 ml of cow cervical blood at 1000×g for 5 minutes, discard supernantant, add equal volume of PBS buffer in blood cells and mix homogeneously, drop the mixture carefully into 3 ml Ficoll-Paque contained in a centrifuge tube without disturbing boundary surface thereof,centrifuge at 2300×g for 25 minutes to result in 4 layers in the tube of which the uppermost layer is PBS buffer, the second layer is leucocytes layer , the third layer consists of Ficoll-Paque, and the lowest layer is the rhodocytes layer. Withdraw leucocytes, wash with twice volume of PBS buffer, centrifuige at 400×g for 5 minutes to settle completely leucocytes at bottom of the tube, and then, obtain high concentrated leucocytes by dissolving pellet with 1 ml PBS buffer.

Next, leucocytes thus-obtained were extracted by means of GENOMIC DNA extraction kit (Talent, Italia) to obtain genomic DNA of high purity.Then, enzymatic amplification was carried out by using the above described two primers, i.e., pbAML5XY(+) and pbAML5XY(-), which reaction was performed at a total volume of 50 $\mu$l with a composition comprising of 100 ng leucocyte DNA template, 100 $\mu$l M dNTPs, 0.1 $\mu$M of primers, 1.25$\mu$ Ta DNA polymerase and 1X PCR buffer (10 mM Tris-HCl, pH9.4, 2 mM MgCl2, 0.1% Triton X-100). Having overlaid with 50 $\mu$l light mineral spirit, the reaction mixture was placed on a heat plate in the PCR reactor and carried out PCR under the above-described reaction conditions (Table 4). Results indicated that all of the 15 female cow samples gave a PCR products of 467-bp, while DNA samples from 6 male Holstein cows gave two PCR products having different length of 467-bp and 341-bp, respectively. This result was coincidental with that predicted. Accordingly, primer pair designed according to the invention can give an accuracy as high as 100% in sexing between male and female.

Furthermore, the sensitivity of the primer pair in sexing was tested by using leucocytes. After a series of dilution, leucocytes was placed under a phase contrast microscope at 400X amplification, drew one to ten of cells with ultrafine glass pipette, placed in a 0.5 ml microcentrifuge tube and frozen in a refrigerator at −70° C. Then, prepared PCR reaction buffer based on the composition shown in Table 3 and carried out enzymatic amplification under conditions described in Table 4. From the result shown in FIG. 4, it was evident that, no matter whether the cow is male or female, leucocytes at a cell number of 8, 6, 4, 2, or 1 can be distinguished un-ambiguously by the primer pair of pbAML5XY(+) and pbAML5XY(-) according to the invention. Consequently, through combination of the primer pair with proper PCR reaction conditions, the sexing sensitivity thereof can achieve an order of one cell. Moreover, since the diameter of the cow embryonic blastomere is much larger than that of the leucocytes, it is feasible to carry out sexing on a single blastomere sampled from a blastula.

EXAMPLE 2

Sexing on a single cow embryonic blastomere.

By means of non-surgical method, flush the uterous cornis at the sixth or seventh day after insemination and obtain un-implanted embryo at morula stage or blastula stage. In order to obtain higher embryo number, every embryo-donating cow had been treated with endocrine so as to achieve the object of superovulation. Such a superovulation treatment comprised of administrating intramuscularly of follicular stimulating hormone (FSH) to the embryo-donating cow sequentially for 4 days since tenth day of estrous cycle twice a day with interval of 12 hours and the dosage was decreased daily as 6-, 5-. 4- and 3-mg, respectively. As the first dosage at the third day, co-administrated with 500 $\mu$g prostaglandin PGF2 α (about 2 ml Estrumate) which resulted in detection of estrous after 48 hours whereupon gave two aftificial insemination with a interval of 12 hours therebetween. Then, at about six or seven days after conception, performed non-surgical embryo flushing, wherein the actual operation of endocrine treatment was proceeded as shown in the time schedule hereinafter.

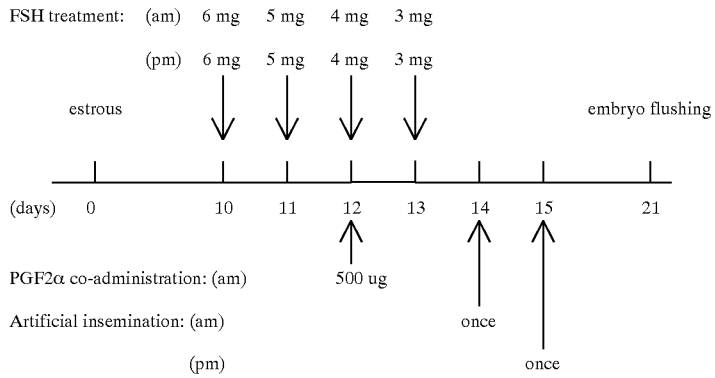

As regard to non-surgical embryo flushing method, the embryo-donating cow was secured on a fixing frame and was injected extradurally at the back base of tail root about 6–8 ml of 2% procaine anesthetic, followed by spray sterile cleaning its externalia with 70% alcohol and bound its tail to prevent it from interfering the flushing. Then, after coating the front end of an embryo flushing cannula previously prepared with lubricant, the operator puts one hand into the rectum and grasps the uteri cervix while the other hand holds the cannula and inserts it through the vagina. When the cannula reached the uteri cervix, removed its outer plastic protective shealth and introduced it slowly into the uterous cornis, then, injected into 10–15 ml of air with a 20-ml syringe to expand the baloon at front end of the embryo flushing cannula so that it could swell against the uterine wall to prevent backflow of the flushing solution. Under these circumstance, the right and left uterous cornis was flushed separately with 250 ml of embryo flushing solution (DPBS) and recovered the solution as shown in FIG. 7. The volumetric cylinder containing the embryo flushing solution recovered was allowed to stand for 15 minutes, and then, drew off the upper layer of the solution recovered with a siphon to leave about 75 ml low layer solution which, after being slightly shaken, was distributed in 10 cm petri dishes and sampled cow embry under stereoscopic microscope.

The cow embryo collected was drawn with a sterile glass capillary tube and was transferred into another petri dish where it was rinsed more than ten times. Thereafter, it was placed under a phase contrast microscope at 400X amplification for sampling of single blastomere at morula or blastula stage, as shown in FIG. 7. The single blastomere obtained was placed directly in a 0.5 ml thin wall microcentrifuge tube and frozen quickly in a refrigerator at −70° C. until PCR sexing. As soon as the single blastomere had been sampled, the cow embry was placed into a DPBS culture medium containing 10% serum and cultivated in a cultivation theremostat at 39° C. to cure the mechanical damage at its zone pellucida.

The preparation of PCR reaction buffer and the PCR reaction conditions uesd in sexing the cow embryo single blastomere were the same as described in Table 3 and 4, respectively. FIG. 5 lists results of sexing blastomeres sampled at the blastula stage, wherein, ♂ and ♀ represent leucocyte control of male and female cows, respectively, and it can be seen obviously that leucocytes from male cows yielded PCR products of 467-bp and 341-bp, whereas leucocytes from female cows yielded only one PCR product having a length of 467-bp. Such cow embryo sexing results shows that blastomeres No. 1, 2, 4, 7 and 9 belong to male embryos, while seven blastomeres derived from different blastulae as No. 3, 5, 6, 8, 10, 11 and 12 were determined as female embryos. Such PCR sexing result has been confirmed by traditional karyotyping analysis and thereby proves the accuracy of PCR sexing method according to the invention.

Advantages and features of the cow embryo sexing method according to the invention comprises:

1. having extremely high sensitivity, that the precise sensitivity of sex-determination was confirmed to be reached as minimum template as trace amount of genomic DNA content in either a single lymphocyte or a single blastomere isolated from cow embryo at day-6 or day-7;
2. having a quick sex diagnosing capability, that the sex-determination of over hundred embryos can be completed at once within 4 hours;
3. a simple and easy operation procedure, that neither those of complicated procedures for purifying the DNA prior the PCR nor any extra pair of primers for serving as an internal control is thought to be essential; and
4. having an accuracy of sex determination as high as 100%.

What is claimed is:

1. An oligonucleotide primer set for bovine embryo sexing wherein said oligonucleotide primer set comprises a primer pair which primer pair consists of individual oligonucleotide primers each of which is able to hybridize specifically and simultaneously to an intron 5 sequence of the bovine amelogenin gene, which gene is located on both the bovine X and Y chromosomes, wherein said intron 5 sequence of the bovine amelogenin gene is selected from the group consisting of: SEQ ID NO: 21 (the nucleotide sequence of intron 5 of the bovine amelogenin gene located on the bovine X chromosome), that sequence fully complementary to SEQ ID NO: 21, SEQ ID NO: 22 (the nucleotide sequence of intron 5 of the bovine amelogenin gene located on the bovine Y chromosome), and that sequence fully complementary to SEQ ID NO: 22.

2. A primer pair, for sex determination of cow embryonic cells, which comprises a DNA sequence selected from the group consisting of:

5'-AAATTCTCTCACAGTCCAAG-3' (SEQ ID NO: 16); and

5'-CAACAGGTAATTTTCCTTTAG-3' (SEQ ID NO: 19).

3. A process for sexing a cow embryo comprising the following steps:

(a) isolating a single cow blastomere by micromanipulation and placing the blastomere sample into a low tonic solution, then heating under 97° C. to denature its proteins and expose its genomic DNA;

(b) carrying out a PCR-sexing reaction by using a primer pair according to claim 2, wherein the concentration of the primer pair is increased from the conventional 100 nM to 400 nM, and the amount of thermostable Taq DNA polymerase in the reaction system is twice (2.5 U) that used in conventional PCR (i.e. 1.25U), and wherein said PCR-sexing reaction is carried out in a program having reaction conditions as follows: 94° C., 30 seconds; 53° C., 1 minute; 72° C., 1 minute repeating 20 cycles; followed by 94° C., 30 seconds; 54° C., 1 minute; 72° C., 1 minute repeating 30 cycles; and with a termination step as 72° C., 5 minutes and 4° C., 2 minutes, whereby PCR products are produced; and (c) size separating said PCR products by electrophoresis, wherein PCR products derived from a female embryo (XX) has a length of 467-bp, while those products derived from a male embryo(XY) have lengths of 467-bp and 341-bp, thereby determining the sex type of the cow embryo.

4. A kit for sexing a cow embryo comprising a primer pair according to claim 1 and at least one reagent for performing PCR.

5. A process for sexing a cow embryo which comprises isolating a cow embryo and exposing its genomic DNA; carrying out PCR sexing reaction using the primer pair of claim 2 as primer to thereby obtain PCR products; and size separating said PCR products whereby the presence of 467 bp and 341 bp PCR products indicates a male embryo and the presence of only 467 bp PCR product indicates the presence of a female embryo.

6. A compound which is a oligonucleotide selected from the group consisting of SEQ ID NO: 14, SEQ ID NO: 16, SEQ ID NO: 19, SEQ ID NO: 21 and SEQ ID NO: 22.

7. A kit for sexing a cow embryo according to claim 4 wherein said at least one reagent is selected from the group consisting of: Taq DNA polymerase, dNTPs and 1X PCR buffer wherein said Taq DNA polymerase is present in an amount of 2.5 U; said dNTPs are present in an amount of 0.2 mM and said 1X PCR buffer contains: 20 mM Tris-HCl having a pH of 8.8, 10 mM $(NH_4)_2$ $SO_4$, 10 mM $MgCl_2$,2 mM $MgSO_4$, 0.1% Triton X-100 and 0.1 mg/ml BSA.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single ( D ) TOPOLOGY: linear ( i i ) MOLECULE TYPE: DNA (genomic)

( x i ) SEQUENCE DESCRIPTION: SEQ ID NO:1:

AAATTCTCTC ACAGTCCAAG                                                                        20

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CAACAGGTAA TTTTCCTTTA G                                                                      21

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

CACTGAGAAC GTGTGTTC                                                                          18

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGGAGGCAGG CAAACAAAA                                                                         19

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ATTTGTTTG CCTGCCTCCT                                                                         20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AGTTGATATA ACCAGGGTGC 20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GCACCCTGGT TATATCAACT 20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GTCTTATCAT GCTCTGGTAC 20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GTACCAGAGC ATGATAAGAC 20

(2) INFORMATION FOR SEQ ID NO:10:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

TCGTAACCAT AGGAAGGG 18

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCAACAGAC AAGACCAAG 19

(2) INFORMATION FOR SEQ ID NO:12:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:12:

TTTACTTCAG GTCTCTTCTC      20

( 2 ) INFORMATION FOR SEQ ID NO:13:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

AGCAACAGAC AAGACCAAG      19

( 2 ) INFORMATION FOR SEQ ID NO:14:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

GTAGAATGAT TATGGGCACA AA      22

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

AAAATCTCTC ACAGTCCAAG      20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

AAATTCTCTC ACAGTCCAAG      20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single -continued (D) TOPOLOGY: linear (i i) MOLECULE TYPE: DNA (genomic)

(x i) SEQUENCE DESCRIPTION: SEQ ID NO:17:

AAATTCTCTC ACAGTCCAAG 20

(2) INFORMATION FOR SEQ ID NO:18:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:18:

AAACAAGTAA TTTTCCTTTA G 21

(2) INFORMATION FOR SEQ ID NO:19:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:19:

CAACAGGTAA TTTTCCTTTA G 21

(2) INFORMATION FOR SEQ ID NO:20:

(i) SEQUENCE CHARACTERISTICS:
(A) LENGTH: 21 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:20:

CAACAGGTAA TATTCCTTTA G 21

(2) INFORMATION FOR SEQ ID NO:21:

(i) SEQUENCE CHARACTERISTICS:
(A) LENGTH: 1684 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:21:

| | | | | | |
|---|---|---|---|---|---|
| GTGAGTATAC | CTTGAGGTCA | CTACAACACT | TATGAAAATG | GTCGAGCGAA | AATGGCCCCC | 60 |
| CCAGAGATTG | AAAATCTCTC | ACAGTCCAAG | GCCTACAGTT | TCAGTAGCTA | CAGCTACAGC | 120 |
| TCAGTGATTC | AGTTAGCCCA | AGTGTGTGCT | GTAAGTTTAT | ATTATAAAGA | GTTCATCTAT | 180 |
| ATGGCTTAGA | ATTAACACAA | TAGCTTTTAT | GGTGGACAGG | GAGGCCTGGC | GTGCTGCGAT | 240 |
| TCATGGGGTC | GTAAAGAGTC | GGACATGACT | GAGCTACTGA | TCTGATCTGA | TCTGAAATTC | 300 |
| TATAATTACT | TTGAATTCCT | ACCAGAATAT | CTATTATTGA | AACCTGTTAA | TTTTACAGAC | 360 |
| AGTACTATAA | GGGAACATTA | GTTCTCTTTA | TCTTTCAAAG | GTTTGACCAG | CAATAATAGG | 420 |

-continued

| | | | | | | |
|---|---|---|---|---|---|---|
| CTAGAATTGA | ACCGGAGATT | TCTTTTAAAA | GGGTAATTTT | TGCCAGTGAG | GGGATGCAGA | 480 |
| TATTTGAACA | GGTAGGTGGG | AGGTCTCTTT | AAAAACCTAA | AGGAAAATTA | CTTGTTTAAA | 540 |
| GTGGTTTTCA | ATCTAACTTG | GAGGAAGCTA | AACTACACAG | ATTGCTAGAT | TCCTTTTCAG | 600 |
| TGCTGGGATT | CTGTAGATTA | AGCTTTTAGC | AATAAGTCTT | CATAGTAAAG | GACAAAATAT | 660 |
| CCTTTCATTA | CAGAAAGCTC | TTTCCCACTC | TTCCAAGTGA | GTGGGAAATA | GTCAATAAGT | 720 |
| GACCCTTATC | CATATATATA | AACCCTCACT | TGTGTGTATA | AGAGATTATG | TAATTCTACT | 780 |
| GTATGCATGT | CTTCAAATGT | AATTCCAAGC | TATAAATGTT | ATTAATGATT | TTCTACTGAG | 840 |
| AAGGTGAGGG | GTGGGGTAGA | AATGACCTGG | ATGGGAGCC | GGGATACCTG | AGTTCCAGTT | 900 |
| ATAACTCTGC | ACTCAAAAAG | GAGATGCTGT | TTAACAAGTC | ACTTCAACTA | TATGGGTGTT | 960 |
| TACCCGTTAA | AATGAGAGGA | AGTAACTAAA | TCAAATAACT | TTCAAGCCTT | TGTCTAAGAA | 1020 |
| GAAATACCAT | AGTTTTCCAA | TAAAAATTAT | ATGTTATATA | AGGCTTCAAA | ATTATGGAA | 1080 |
| TATTTGTGGA | GAACACAGGC | ATATTTGTGG | AAAATATGGA | GCATATTTGA | AAAATGATTG | 1140 |
| TATCCCAAAT | GCTCTGGTGC | CTACAGTTGA | TTATTCTAGT | CTAAGGTACA | GGTTACGTCT | 1200 |
| TTGTATAGAA | AATATGTTTA | TCTCGCCAAA | ATGCATTTAT | CTCTTTATTA | ATAATTAGTG | 1260 |
| TTATGAACTT | TATAAATCTT | GCCAGAGCTA | TTCAAGGAAA | GGTGATTTTG | GGTACGTAGT | 1320 |
| TTGAACTCTT | TAAAATTCCC | ATCTAAAATT | AGAGGTAAAT | AGTGATAGCA | TCTTAGAGTT | 1380 |
| GTCTTAAGAA | AATAAAGTGT | TGAGTTTAAG | AAATGACCAT | GCAGAAAGTA | CTCACCCCAA | 1440 |
| TACAGCAATT | GTTGTTTTAT | TATTCAATAA | TTGTTTTAAG | TATTCTGAAG | GCAGGGGCCT | 1500 |
| CCATCCTGAC | ACCTCATATC | TAATGACTAT | GAGACAACAA | AGAAAGTTTG | TGAATTATAG | 1560 |
| AGTCCAACTT | CAATGGCTAT | AATATTGTTT | TGGCAAAATT | GAACCCATAT | TTGTTACTAT | 1620 |
| AAATGGTACT | CACTAAGAAT | ATTTGTAAAT | TGTTTTACTT | GCTTCTTTTG | CAATTTTTTT | 1680 |
| CCAG | | | | | | 1684 |

( 2 ) INFORMATION FOR SEQ ID NO:22:

( i ) SEQUENCE CHARACTERISTICS:
        ( A ) LENGTH: 1539 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

| | | | | | | |
|---|---|---|---|---|---|---|
| GTAAGTACAC | CTTAAGGCCA | TTTACAACAG | TTATGAAAAT | AATCGAGCAA | AAATAGCCCA | 60 |
| CAGAAATCAA | AATTCTCTCA | CAGTCCAAGA | CCTAGAGTTT | CAACTGCAGT | TAGTGATTCT | 120 |
| ATTATTCCAA | GTGTGTGTTG | TAAGTTTATA | AATGAGCTTG | TTTATCTATA | TGGCATACAC | 180 |
| TTTGTGAATT | CAAAATCTAC | AATTGTTTGG | AATTTAATG | GCAATATGAA | TTGCTATTGA | 240 |
| AATGCAGTAT | AATAAAGGCA | ACAATTCTTA | TCTTCTGGTT | GCTTAACTAG | TACATTAGAC | 300 |
| TTATACAGAA | ATAAATAAAA | AGAGTATTTC | TGGGATTGAG | GAGAAGGAAG | TATCAGTTTT | 360 |
| AAAAAATTAT | AGCTGGATCT | TCAAGGCTCT | AAAGGAATAT | TACCTGTTGT | AGGTGGTTTT | 420 |
| AAAGTAATTT | GGAAACAGTT | AAAGTAGACA | AACGTAGATT | CTATTTCATT | CCCAGGATTA | 480 |
| AAAAAAATTT | TAATAAGAAT | GTTTCATAAC | ATAGCTTAAA | ATTTCCTCCC | CACTTCAGAA | 540 |
| ATCTTTTGGG | GAATAATTGA | GAAGTAACCC | AATAAGGGTC | ACCTTCCATT | CATTCCTGTA | 600 |
| AACCCTCATT | TCTCTGCATT | AAGTTTAGTA | ATTCTACAAT | TAATAAATGC | TGTTAGGGAT | 660 |
| TTGCTACTGA | GAAAACACTG | AAGAGTAAGG | TAGAAATAAC | CTGAATATAT | AGTCAGGATA | 720 |

-continued

| | | | | | | |
|---|---|---|---|---|---|---|
| TGTGGCTTCT | ATTGCTAGCT | CTGCCCTGAA | GAAGAAATTT | ACAGCTGTTT | TCCTCTAAAT | 780 |
| GTTTCCTCTA | AATTGGTTTT | CCTCTCTCCT | AAAATAAGTG | AAAGTGATCA | GTTTAAAGGC | 840 |
| TCTTTGCAAG | TATTTGTGCT | TAGAGTACAA | AGAGTAAAAT | ATTTTATGTT | CATTATTTAA | 900 |
| AAGTTAAAAT | ATTCAATTAA | TCAAAATATT | TTATTATTAA | ATATAATTTC | CCAATAAAAA | 960 |
| ATTTTTATAA | ACCATATCAT | AATTTTGGTA | CATTTATGAG | AAATTGTGAC | TGTTTGAAAA | 1020 |
| TTGATTGTAT | CCCAAACATT | GTGGTACCAA | TGACTATTTC | AGTCTAACCT | ACATGGGCTC | 1080 |
| TGATTAAATA | GAAGATACAT | TTCTTTGTTC | ATTAACAAAT | AATGTCATGG | AATTTACAGT | 1140 |
| ATGTTTATAT | CATGTCAAAG | ATATGCATGT | AAAGATGCTC | TGGTTAGGTA | AACTCTTAAA | 1200 |
| ATTTCATTTC | TGCTTCTGGA | AAATTAGGAT | AAATGGATCT | TCTTAGAATT | ATTTATAGAA | 1260 |
| AAATGGATCT | TCTTAGAATT | ATTTATAGAA | AATGATATAA | AATTATTAAC | TATTAGGGAC | 1320 |
| AGGTCAGAAA | AAAATCGGTG | TGTTACTCAA | ATTATCGATG | GTTGTAAAGG | TTTTAAAGCA | 1380 |
| GGGCTGCCCA | CATAGACACT | TCAAATATAA | TGATAAAGTG | ACAAACCTTT | TGGAAATTAT | 1440 |
| AAATTTTAAC | TTACTGGTTA | CCATCTTTTC | TAGTAAAACT | GAAGATGGAT | TCTCTAGTAA | 1500 |
| TATTTGTAAA | TTACATGTTC | ATTTTGTTTT | TTTCCCCAG | | | 1539 |